United States Patent [19]

Menendez et al.

[11] Patent Number: 4,882,170

[45] Date of Patent: Nov. 21, 1989

[54] METHOD OF TREATMENT

[75] Inventors: Rogelio Menendez, Nashua, N.H.; Kenneth J. Gorelick, Winchester, Mass.

[73] Assignee: Fisons Corporation, Bedford, Mass.

[21] Appl. No.: 28,451

[22] Filed: Mar. 20, 1987

[51] Int. Cl.$^4$ ................ A61K 33/00; A61K 31/35
[52] U.S. Cl. .................... 424/600; 514/456; 514/816
[58] Field of Search ............ 514/456, 816; 424/45

[56] References Cited

U.S. PATENT DOCUMENTS

| | | | |
|---|---|---|---|
| 3,686,412 | 8/1972 | Fitzmaurice et al. | 514/456 |
| 3,957,965 | 5/1976 | Hartley et al. | 514/456 |
| 4,080,389 | 3/1978 | Moilliet | 514/816 |
| 4,192,860 | 3/1980 | Griffiths | 514/456 |

Primary Examiner—Douglas W. Robinson
Assistant Examiner—R. Kearse
Attorney, Agent, or Firm—Marshall, O'Toole, Gerstein, Murray & Bicknell

[57] ABSTRACT

There is described a method for the prevention or inhibition of an allergic reaction or tissue inflammation resulting from the placement of an endotracheal instrument or device, which method comprises administration by inhalation of an anti-allergy drug to a patient prior to the placement, during the placement, or while the instrument or device is in place.

There are also described pharmaceutical mixtures comprising, as a first component, an anti-allergy drug and, as a second component, a substance conventionally administered by endotracheal intubation.

11 Claims, No Drawings

METHOD OF TREATMENT

BACKGROUND OF THE INVENTION

This invention relates to a new therapeutic method and pharmaceutical mixtures for use therein.

It is known that placement of an endotracheal instrument or device may, particularly in the case of patients with a history of chronic atopy, bring about an adverse reaction. Such an adverse reaction may take the form of an allergic reaction or tissue inflammation or both.

BRIEF SUMMARY OF THE INVENTION

We have now found that administration by inhalation of an anti-allergy drug to a patient prior to and/or during placement of an endotracheal instrument or device, and/or whilst said instrument or device is in place may substantially lessen the probability that the patient will suffer such an adverse reaction.

Thus according to the invention there is provided a method for the prevention or inhibition of an allergic reaction or tissue inflammation resulting from the placement of an endotracheal instrument or device, which method comprises administration by inhalation of an anti-allergy drug to a patient prior to the placement, during the placement, or whilst said instrument or device is in place.

DETAILED DESCRIPTION OF THE INVENTION

Specific procedures involving the placement of an endotracheal instrument or device which may be mentioned include bronchoscopy, tracheoscopy and endotracheal intubation for the purpose of positive pressure ventilation, for the bypassing of obstructions of the airways or for the administration of gases, e.g. anaesthetic gases.

The drug may be formulated either in finely divided form as a pressurised aerosol pack or as a powder formulation in combination with a coarse carrier, e.g. lactose.

We prefer, however, that the drug be made up as an aqueous solution and be administered as a nebulised cloud. The aqueous solution preferably contains from about 0.1 to 10%, more preferably 0.1 to 2%, e.g. about 1% by weight of the drug.

The dosage to be administered will vary inter alia with the mode of administration. However, in general a dosage of up to about 50 mg of the drug, preferably 10 to 40 mg, e.g. 20 mg (2 ml of a 1% solution), is found to be satisfactory.

When the drug is administered as a nebulised cloud during administration of a gas, e.g. an anaesthetic gas, the nebulisation may be driven by the gas, i.e. the nebulised cloud may be generated by passing the gas through a nebulisation unit containing a solution of the anti-allergy drug.

According to the invention we also provide a mixture comprising, as a first component, an anti-allergy drug and, as a second component, a substance conventionally administered by endotracheal intubation.

The proportions of the first and second components will vary according to the specific components chosen, but in general a sufficient proportion of the first component should be used to inhibit or mitigate any adverse effects arising from intubation and the administration of the second component. In certain circumstances very small proportions of the first component, for example a weight ratio of first component to second component of between 1:2000 and 1:100, preferably between 1:1500 and 1:200, and more preferably between 1:1000 and 1:400, may be sufficient.

Specific substances conventionally administered by endotracheal intubation which may be mentioned include oxygen and inhalation anaesthetics such as chloroform, ether, fluoroxene, halothane, methoxyfluorane, nitrous oxide, trichloroethylene and mixtures of any two or more thereof. The anaesthetic will be administered at the normal dosage used to provide anaesthesia and may be administered in admixture with oxygen or nitrous oxide.

We prefer the anti-allergy drug to be a drug which functions by preventing or inhibiting the release of factors which mediate the allergic or inflammatory reaction.

A particularly preferred anti-allergy drug for use in this invention is the disodium salt of 1,3-bis(2-carboxychromon-5-yloxy)-2-hydroxypropane, which salt is commonly known as sodium cromoglycate or cromolyn sodium.

Specific adverse reactions in the prevention of which the present invention is useful are those associated with an increase in histamine in the blood, or with a fall in blood pressure, or with urticaria, or with bronchospasms or with post-operative stress ulcers (increased gastric acid secretion) or with white blood cell changes. These adverse reactions may, in extreme cases, take the form of anaphylactic shock.

The invention is illustrated, but in no way limited, by the following Examples.

EXAMPLE 1

A patient was admitted to hospital 24 hours prior to an elective hernia repair. On the morning of the operation the patient received standard pre-medication with OMNOPON (Omnopon is a trade mark) and scopolamine approximately one and a half hours before being transferred to the operating theatre. The patient was transferred to the anaesthetic room attached to the theatre and while final preparations for the anaesthetic were being made the patient received 20 mg of sodium cromoglycate in the form of an aqueous solution delivered by standard gas-driven nebuliser with a plastic face-mask. After 5 minutes of nebulisation the patient received an intravenous injection of thiopentone, the endotracheal tube was placed and anaesthetisation continued with a nitrous oxide/oxygen mixture. Anaesthesia, operation and recovery then proceeded smoothly and uneventfully.

EXAMPLE 2

A patient was admitted to hospital as an emergency having been found at home collapsed and unconscious. On arrival at hospital the patient was unconscious, breathing spontaneously but shallowly with restricted ventilation and was cyanosed. An endotracheal tube was inserted and the patent was administered 20 mg of sodium cromoglycate as an aqueous solution from a gas-driven nebuliser which was connected in series with the ventilator. The administration of sodium cromoglycate was repeated six-hourly throughout the forty-eight hour period during which the patient required ventilation.

We claim:

1. A method for the inhibition of an allergic reaction or tissue inflammation resulting from the placement of an endotracheal instrument or device, which method comprises the steps of (a) administration by inhalation of cromolyn sodium to a patient, and (b) placement of the endotracheal instrument or device, steps (a) and (b) being performed in any order or simultaneously.

2. A method according to claim 1, wherein the cromolyn sodium is administered as a nebulised cloud of an aqueous solution.

3. A method according to claim 2, wherein the solution contains from 0.1 to 10% w/v of cromolyn sodium.

4. A method according to claim 2, wherein the solution contains from 0.1 to 2% w/v of cromolyn sodium.

5. A method according to claim 2, wherein the nebulised cloud is generated by passing a gas to be administered to the patient through a nebulisation unit containing the aqueous solution of the cromolyn sodium.

6. A pharmaceutical composition comprising, as a first component, cromolyn sodium in a proportion effective for the inhibition of an allergic reaction or tissue inflammation resulting from the placement of an endotracheal instrument or device and, as a second component, a general inhalation anaesthetic wherein the weight ratio of first component to second component is from 1:2000 to 1:100.

7. A composition according to claim 6, wherein the weight ratio of first component to second component is from 1:1500 to 1:200.

8. A composition according to claim 6, wherein the weight ratio of first component to second component is from 1:1000 to 1:400.

9. A composition according to claim 6, wherein the second component is nitrous oxide.

10. A composition according to claim 6, wherein the second component is halothane.

11. A composition according to claim 6, wherein the second component is chloroform.

* * * * *